(12) United States Patent
Suh et al.

(10) Patent No.: US 9,040,580 B2
(45) Date of Patent: May 26, 2015

(54) METHOD FOR PREVENTION OR TREATMENT OF DEGENERATIVE NEUROLOGIAL BRAIN DISORDERS

(75) Inventors: Yoo-Hun Suh, Seoul (KR); Sushruta Koppula, Chungju-si (KR); Su-Jin Noh, Seoul (KR)

(73) Assignee: BRAINTROPIA CO., LTD., Anyang-Si Gyeonggi-Do (KR)

( * ) Notice: Subject to any disclaimer, the term of this patent is extended or adjusted under 35 U.S.C. 154(b) by 95 days.

(21) Appl. No.: 13/820,520

(22) PCT Filed: May 18, 2011

(86) PCT No.: PCT/KR2011/003669
§ 371 (c)(1),
(2), (4) Date: Mar. 3, 2013

(87) PCT Pub. No.: WO2012/030050
PCT Pub. Date: Mar. 8, 2012

(65) Prior Publication Data
US 2013/0178527 A1     Jul. 11, 2013

(30) Foreign Application Priority Data
Sep. 3, 2010   (KR) .................... 10-2010-0086280

(51) Int. Cl.
*A61K 31/235*     (2006.01)

(52) U.S. Cl.
CPC .................... *A61K 31/235* (2013.01)

(58) Field of Classification Search
CPC .................................................. A61K 31/235
See application file for complete search history.

(56) References Cited

U.S. PATENT DOCUMENTS

| 5,017,607 | A | 5/1991 | Chiesi | |
| 6,630,507 | B1* | 10/2003 | Hampson et al. | 514/454 |
| 2006/0210652 | A1* | 9/2006 | Kim et al. | 424/725 |

FOREIGN PATENT DOCUMENTS

| KR | 10-2002-0084311 A | 11/2002 |
| KR | 10-2005-0062574 A | 6/2005 |
| KR | 10-2007-0092497 A | 9/2007 |
| KR | 10-2009-0048934 A | 5/2009 |
| WO | 9630012 A1 | 10/1996 |

OTHER PUBLICATIONS

Korotkova et al. Electrochimica Acta, 2005, vol. 51, pp. 324-332.*
Miyake et al. European Journal of Neurology, 2011, vol. 18, No. 1, pp. 106-113 (Abstract attached).*
Fernandez-Calle et al. (J. Neurol. Sci., 1994, vol. 124, No. 1, pp. 113-114 (Abstract attached).*
Snow et al. Movement Disorders, 2010, vol. 25, No. 11, pp. 1670-1674.*
Carlson et al. CNS Drugs, 2006, vol. 20, No. 6, pp. 433-441.*
Ebadi et al. Progress in Neurobiology, 1996, vol. 48, pp. 1-19.*
International Search Report for PCT/KR2011/003669.

* cited by examiner

*Primary Examiner* — James D Anderson
(74) *Attorney, Agent, or Firm* — Hultquist, PLLC; Steven J. Hultquist; Mary B. Grant

(57) ABSTRACT

The present invention relates to a method for the prevention or treatment of degenerative neurological brain disorders and, more specifically, relates to a method for the prevention or treatment of degenerative neurological brain disorders, such as Parkinson's disease, Alzheimer's dementia (senile dementia), stroke, Lou Gehrig's disease, Pick's disease, Creutzfeldt-Jakob disease, Huntington's disease, progressive supranuclear palsy, spinocerebellar degeneration, cerebellar atrophy, multiple sclerosis, post-traumatic stress disorder, and amnesia. The method includes administering to a subject in need thereof a therapeutically effective amount of a composition, wherein the composition contains a paraben compound as an active ingredient having effects that are useful in combating oxidation to remove active oxygen, suppressing cell-death, improving impaired movement, and enhancing declining memory.

3 Claims, 6 Drawing Sheets

METHOD FOR PREVENTION OR TREATMENT OF DEGENERATIVE NEUROLOGIAL BRAIN DISORDERS

CROSS REFERENCE TO RELATED APPLICATIONS AND CLAIM OF PRIORITY

This patent application is a National Phase application under 35 U.S.C. §371 of International Application No. PCT/KR2011/003669, filed May 18, 2011, which claims priority to Korean Patent Application No. 10-2010-0086280 filed Sep. 3, 2010, entire contents of which are incorporated herein by reference.

BACKGROUND

1. Technical Field

The present invention relates a pharmaceutical composition for prevention or treatment of degenerative neurological brain disorders, such as Parkinson's disease, Alzheimer's dementia (senile dementia), stroke, Lou Gehrig's disease, Pick's disease, Creutzfeldt-Jakob disease, Huntington's disease, progressive supranuclear palsy, spinocerebellar degeneration, cerebellar atrophy, multiple sclerosis, post-traumatic stress disorder, and amnesia.

2. Description of the Related Art

Degenerative neurological brain disorders representative by Parkinson's disease, Alzheimer's disease, dementia, stroke, etc. are well known to be derived from cell death followed by damage and loss of nerve cells ('neurons'), as an ultimate cause. For instance, in the case of Parkinson's disease, dopaminergic neurons present in substantia nigra of mesencephalon are selectively lost so as to cause dysfunction of basal nuclei participating in movement functional tissues, and lead to continuous trembling, stiffness, slow oscillation, unstable posture, etc. (Nimi et al., Clinical and physiological characteristics of autonomic failure with Parkinson's disease. Clin Autonom Res 9(1999), 139-144; Dawson et al., Molecular pathways of neurodegeneration in Parkinson's disease. Science (2003), 819-822).

Active oxygen is indicated as a major cause of neuron death in relation to degenerative neurological brain disorders. This active oxygen refers to oxygen having strong oxidation activity, which is received in a living body during breathing and used for oxidation, generated in different metabolic processes, attacks bio-tissues in the body and damages cells. Such active oxygen may cause irreversible damage in DNA, cell formable proteins and lipids in living cells (Valko et al., Free radicals and antioxidants in normal physiological functions and human disease. Int J Biochem Cell Biol. 39(2007), 44-84). In particular, when active oxygen is generated in a large quantity in brain cells, oxidative stress occurs and causes changes in the structure and function of mitochondria in the cell, in turn causing neurological brain disorders such as Parkinson's disease, Alzheimer's disease, etc. (Knott et al., Mitochondrial fragmentation in neurodegeneration. Nat Rev Neurosci., 9(2008), 505-18).

Alternatively, with respect to degenerative neurological brain disorders including Parkinson's disease, a lot of study results regarding the role of glutamate as an excitatory neurotransmitter and an abnormally accumulated protein have been reported. It is now known that glutamate performs a physiologically important role but, when it is excessively secreted, may cause damage of neurons, thus being party to the cause of specific diseases, i.e., degenerative neurological brain disorders including Parkinson's disease. (Samuel et al., Localization of N-methyl-D-aspartate receptors in the rat striatum: effects of specific lesions on the [3H] 3-(2-carboxypiperazin-4-yl)propyl-1-phosphonic acid binding. J Neurochem 1990; 54:1926-1933; Weihmuller et al., Elevated NMDA receptors in Parkinsonian striatum. Neuroreport 1992; 3:997-980). Furthermore, abnormal accumulation of protein which is characteristic of degenerative neurological brain disorders can be observed. For example, in the case of Parkinson's disease, it was discovered that α-synuclein protein is a major component to form a pathogenic probe of Parkinson's disease, i.e., Lewy body (Spillantini et al., Alpha-synuclein in Lewy bodies. Nature 388(1997), 839-840). The protein described above may be toxic by itself or indirectly express toxicity by generating active oxygen, to hence cause cell death ('apoptosis').

Currently, a method for treatment of Parkinson's disease has yet to be developed and a dopamine precursor, L-dopa or dopamine receptor promoter, is simply known to function as a symptom enhancer. However, this treatment drug cannot prevent continuous loss of dopaminergic neurons and, as a result, may involve a sharp deterioration of efficacy within 5 to 6 years. In addition, side effects including movement dysfunction are increased and L-dopa problems known as 'on-off phenomenon' at the late period of a disease are greatly increased, hence leading to death within 10 to 15 years after the onset of symptoms (Vautier S, Milane A, Fernandez C, Buyse M, Chacun H, Farinotti R, Interactions between antiparkinsonian drugs and ABCB1/P-glycoprotein at the blood-brain barrier in a rat brain endothelial cell model. Neurosci Lett. 442(2008), 19-23; Molecular mechanisms of 6-hydroxydopamine-induced cytotoxicity in PC12 cells: Involvement of hydrogen peroxide-dependent and -independent action. Free Radical Biology & Medicine 42(2007), 675-685).

Meanwhile, it is well known that Parkinson's disease generally includes movement dysfunction as a representative symptom. Moreover, cognitive impairments of varied levels, including dysfunction of autonomic nervous system, sensory nervous system disorders and dementia, are also observed (Morris et al., Planning and spatial working memory in Parkinson's disease. J Neurol Neurosurg Psychiatry, (1988) 757-66; Robbins et al., Cognitive deficits in progressive supranuclear palsy, Parkinson's disease, and multiple system atrophy in tests sensitive to frontal lobe dysfunction. J Neurol Neurosurg Psychiatry, (1994) 79-88). Such cognitive impairments have traditionally been ignored and undervalued since Parkinson's disease has been considered to be a disease involving movement dysfunction. However, cognitive impairments or dementia expressed by a patient with progressive Parkinson's disease are currently considered to be obvious abnormal findings that appear in Parkinson's disease (Emre, Dementia associated with Parkinson's disease. Lancet Neurol., (2003) 229-37; Emre, Dementia in Parkinson's disease: cause and treatment. Curr Opin Neurol., (2004) 399-404). In fact, it is known that about 20 to 40% of Parkinson's disease patients suffer from dementia and the incidence of the dementia is up to 6 times higher than in healthy persons (Mortimer et al., Relationship of motor symptoms to intellectual deficits in Parkinson's disease. Neurology, (1982) 133-7; Emre, Dementia associated with Parkinson's disease. Lancet Neurol., (2003) 229-37).

However, according to conventional studies, it has been reported that the administration of Levodopa (L-dopa) for the improvement of cognitive function in dementia accompanying Parkinson's disease has not been conducted on a large scale. Improvement and positive activity with regards to mood, as well as beneficial effects useful in information processing by dopaminergic neurotransmission and working memory, are partially demonstrated. However, it is known that the main goal, that is, delayed deterioration of cognitive function, cannot be achieved (Pillon et al., Cognitive deficits and dementia in Parkinson's disease. 2 ed. Amsterdam; Elsevier Science; 2001).

Accordingly, it is now urgently required to develop a drug for nerve protective treatment which is capable of preventing or delaying the progress of a disease and a drug for improvement of various degenerative neurological brain disorders as well as dementia symptoms of Parkinson's disease, on the basis of a correct molecular pathological mechanism of Parkinson's disease.

SUMMARY

As a result of intensive study repeatedly executed for prevention or treatment of degenerative neurological brain disorders such as Parkinson's disease, the inventors have found that a compound represented by Formula 1 has a strong removal effect with regards to active oxygen, neuron protection effect, improvement of movement dysfunction, and enhancement of deteriorated memory, and therefore, the present invention has been completed on the basis of the above finding.

An aspect of the present invention is to provide a pharmaceutical composition for the prevention or treatment of degenerative neurological brain disorders, such as Parkinson's disease, Alzheimer's dementia or Lou Gehrig's disease having a pathological mechanism in common with Parkinson's disease, Pick's disease, Creutzfeldt-Jakob disease, Huntington's disease, progressive supranuclear palsy, spinocerebellar degeneration, cerebellar atrophy, multiple sclerosis, senile dementia occurring due to a loss of neurons, stroke, post-traumatic stress disorder, and amnesia.

In order to accomplish the above aspect, there is provided a method for prevention or treatment of degenerative neurological brain disorders by administering to a subject in need thereof a therapeutically effective amount of a pharmaceutical composition, which contains a compound represented by Formula 1 below:

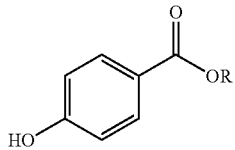

[Formula 1]

(wherein R is an alkyl group having 1 to 6 carbon atoms).

The compound represented by Formula 1 may be at least one selected from a group consisting of methylparaben, ethylparaben, propylparaben, butylparaben, isopropylparaben, and isobutylparaben.

The compound represented by Formula 1 is preferably methylparaben.

The pharmaceutical composition according to an embodiment of the present invention containing a compound represented by Formula 1 exhibits an antioxidant effect to remove active oxygen and suppression of apoptosis caused by α-synuclein, active oxygen and an excitatory neurotransmitter, and is useful for improving movement dysfunction and enhancing deteriorated memory.

In addition, the pharmaceutical composition of the present invention is efficiently used for prevention or treatment of degenerative neurological brain disorders such as Parkinson's disease, Alzheimer's dementia or Lou Gehrig's disease having a pathological mechanism in common with Parkinson's disease, Pick's disease, Creutzfeldt-Jakob disease, Huntington's disease, progressive supranuclear palsy, spinocerebellar degeneration, cerebellar atrophy, multiple sclerosis, senile dementia occurred by loss of neurons, stroke, post-traumatic stress disorder, and amnesia.

DETAILED DESCRIPTION

Figure 1:
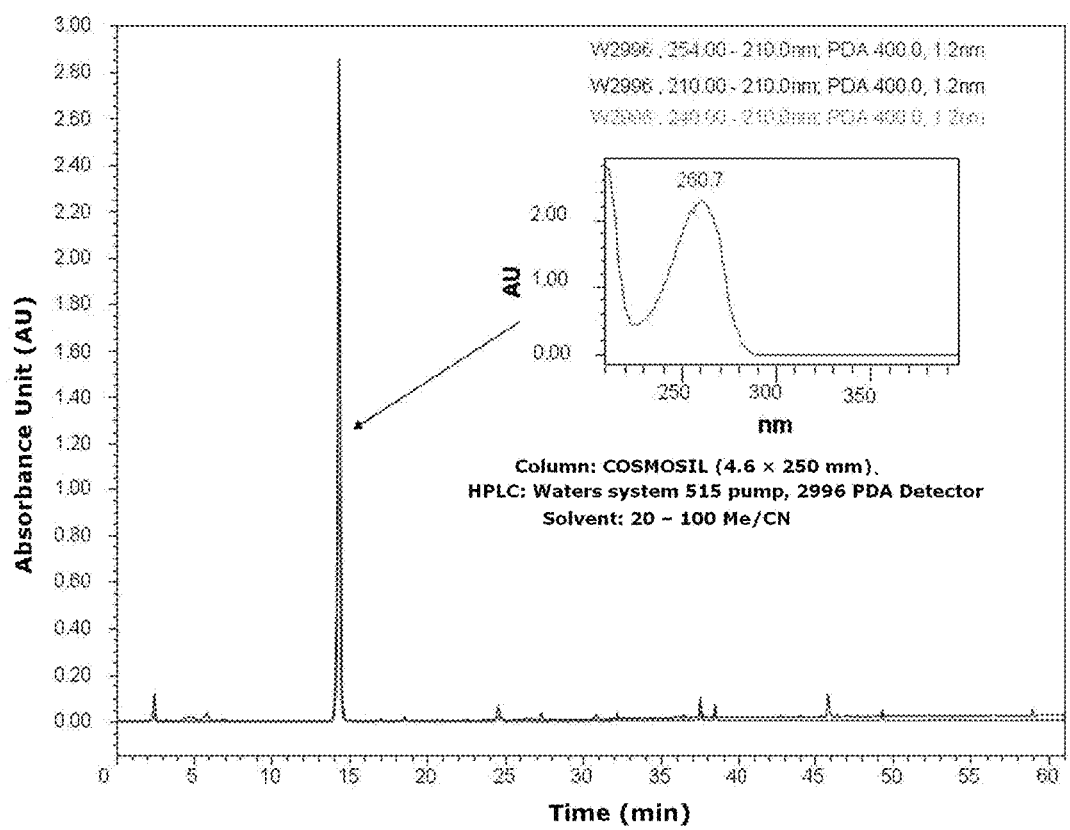
FIG. 1 is an HPLC analysis graph of methylparaben.

The present invention relates to a pharmaceutical composition for the prevention or treatment of degenerative neurological brain disorders, such as Parkinson's disease, Alzheimer's dementia, stroke, Pick's disease, Creutzfeldt-Jakob disease, Huntington's disease, progressive supranuclear palsy, spinocerebellar degeneration, cerebellar atrophy, multiple sclerosis, post-traumatic stress disorder, and amnesia, wherein the composition includes paraben represented by Formula 1 having various effects of removing active oxygen, protecting neurons, improving movement dysfunction, and enhancing deteriorated memory.

Hereinafter, the present invention will be described in detail.

A pharmaceutical composition for prevention or treatment of degenerative neurological brain disorders according to an embodiment of the present invention includes a compound represented by Formula 1 below:

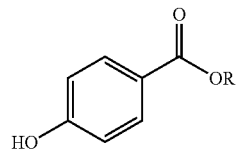

[Formula 1]

(wherein R is an alkyl group having 1 to 6 carbon atoms).

The compound represented by Formula 1 is a paraben compound wherein paraben refers to para-hydroxybenzoate (p-hydroxybenzoate) and has been used as a preserving agent or preservative in foodstuffs (jams, soy sauce, vinegar, drinks, sauce, fruits, vegetables, etc.), medicine and medical supplies, or cosmetics, on the basis of microorganism growth inhibitory effects at a concentration not harmful to a human body.

However, according to an embodiment of the present invention, the compound represented by Formula 1 may be utilized as an effective ingredient of the pharmaceutical composition for the prevention or treatment of degenerative neurological brain disorders, based on the finding of novel activities and effects (i.e., antioxidant effect to remove active oxygen, suppression of cell-death or apoptosis caused by α-synuclein, active oxygen and an excitatory neurotransmitter, neuron protection, improvement of movement dysfunction, and enhancement of deteriorated memory) in the above compound represented by Formula 1, that is, the paraben compound.

The compound represented by Formula 1 may include, for example, methylparaben, ethylparaben, propylparaben, butylparaben, isopropylparaben, and isobutylparaben, which are represented by Formulae 2 to 7, respectively. More particularly, methylparaben represented by Formula 2 below may be used. These compounds may be used alone or in combination with two or more thereof.

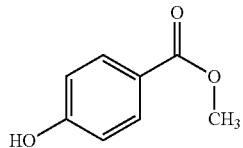
[Formula 2]

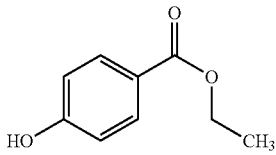
[Formula 3]

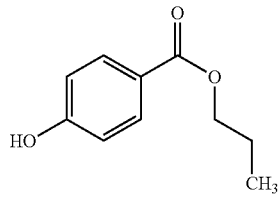
[Formula 4]

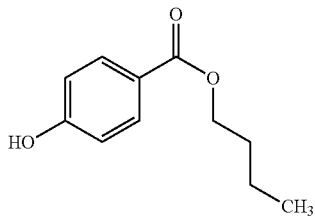
[Formula 5]

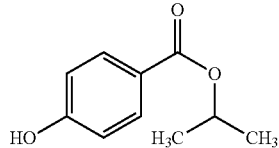
[Formula 6]

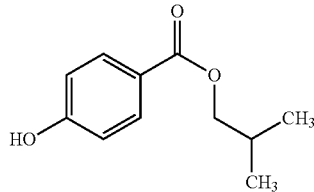
[Formula 7]

The compound represented by Formula 1 needs no specific preparation method. For instance, after reacting phenol with carbon dioxide at high temperature and high pressure, the reaction product may be esterified using alcohol, thus obtaining the above compound in a synthesized state. Alternatively, the above compound may also be isolated from horny goat weed (*Epimedium Koreanum* Nakai) extract or blueberry (*Vaccinium corymbosum*) extract.

A method of isolating the compound represented by Formula 1 from the extract of a natural material is not particularly limited. However, for example, after finely grinding a dried natural material, the ground material is solvent-extracted by any extraction method such as hot water extraction, cold dipping extraction, ultrasonic extraction, reflux-cooling extraction, extraction using decoction vessel, or the like, and using an alcohol solution in an amount of about 2 to 20 times the weight of the ground material. Thereafter, the solvent extract is subject to solvent fraction then chromatography in a silica-gel column, thus being separated.

According to an embodiment of the present invention, the compound represented by Formula 1 used herein may include products purchased by Sigma Co. and other products commercially available from various reagent manufacturers.

The degenerative neurological brain disorders described in the present invention may be any one selected from Parkinson's disease, Alzheimer's dementia or Lou Gehrig's disease having a pathological mechanism in common with Parkinson's disease, Pick's disease, Creutzfeldt-Jakob disease, Huntington's disease, progressive supranuclear palsy, spinocerebellar degeneration, cerebellar atrophy, multiple sclerosis, senile dementia occurred by loss of neurons, stroke, amnesia and post-traumatic stress disorder, in a single form or combination thereof.

The pharmaceutical composition of the present invention may be formulated according to any conventional method. For instance, types of formulation may include granulates, powders, syrups, solutions, suspensions, tablets, capsules, troches or pills for oral administration, or a percutaneous absorption agent, lotions, ointments, adhesive plasters, cataplasma, pastes, suspensions, solutions, injections, or suppositories for parenteral administration.

In addition, the pharmaceutical composition described herein may further include any suitable carrier or excipient generally used in the art. The carrier used herein may include a pharmaceutically acceptable material, for example, water, saline, a buffered solution such as phosphoric acid, acetic acid, citric acid, tartaric acid and other buffered solution to form a solution or suspension, or a liquid, solid or semi-solid carrier containing natural or synthesized bio-degradable polymers or copolymers. The excipient used herein may include, for example: a diluent such as microcrystalline cellulose, lactose, starch, calcium carbonate, glucose, dextrose, dibasic calcium phosphate dehydrate, tribasic calcium phosphate, kaolin, malto-dextrin or mannitol; a binder such as acacia, alginic acid, carbomer, sodium carboxymethyl cellulose, ethyl cellulose, gelatin, guar gum, hydroxyethyl cellulose, hydroxypropyl cellulose, hydroxypropylmethyl cellulose, malto-dextrin, methyl cellulose, polymethacrylate, povidone or sodium alginate; a disintegrant such as gelled starch, alginic acid, calcium carboxymethyl cellulose, croscamellose sodium, crospovidone or sodium starch glycolate; a chelating agent and antioxidant such as alcohol, sodium benzoate, butylated hydroxytoluene, butylated hydroxyanisole or ethylenediamine tetraacetate; an antibiotic agent such as methylparaben or propylparaben; a buffer such as gluconic acid, lactic acid, citric acid or acetic acid, sodium gluconate, sodium lactate, sodium citrate or sodium acetate; a colorant such as titanium dioxide, ferrous oxide or ferric oxide; a sweetener or spice such as sucrose or aspartame, and so forth.

An amount of the effective ingredient in the pharmaceutical composition according to an embodiment of the present invention may be determined by physicians or those skilled in the art and varied depending upon condition, weight and severity of illness of patients, drug type, functions of liver and kidney, administration route and period. For instance, a paraben compound as an effective ingredient may be administered in a dose of 100 to 200 µg/kg once or several times per each day. The World Heath Organization (WHO) has established a daily proper intake of the paraben compound, i.e., methylparaben, ethylparaben and/or propylparaben, of 10 mg/kg.

Hereinafter, exemplary embodiments are proposed to more concretely describe the present invention. However, the following examples are only given for illustrating the present invention and those skilled in the art will obviously understand that various alterations and modifications are possible within the scope and spirit of the present invention. Such alterations and modifications are duly included in the appended claims.

EXAMPLE

Example 1

Synthesis of Methylparaben

After reacting phenol and carbon dioxide at 100 atms and 125° C., sulfuric acid was added thereto to produce parahydroxy benzoate. This compound was esterified using s methanol to synthesize methylparaben (MP).

The synthesized methylparaben (MP) was analyzed by high-performance liquid chromatography (HPLC) and results thereof are shown in FIG. 1.

Further, the synthesized methylparaben (MP) was diluted in phosphate buffered saline (PBS) and used for test and analysis.

Example 2

Hydroxyl Radical Removal Ability Test

Figure 2:
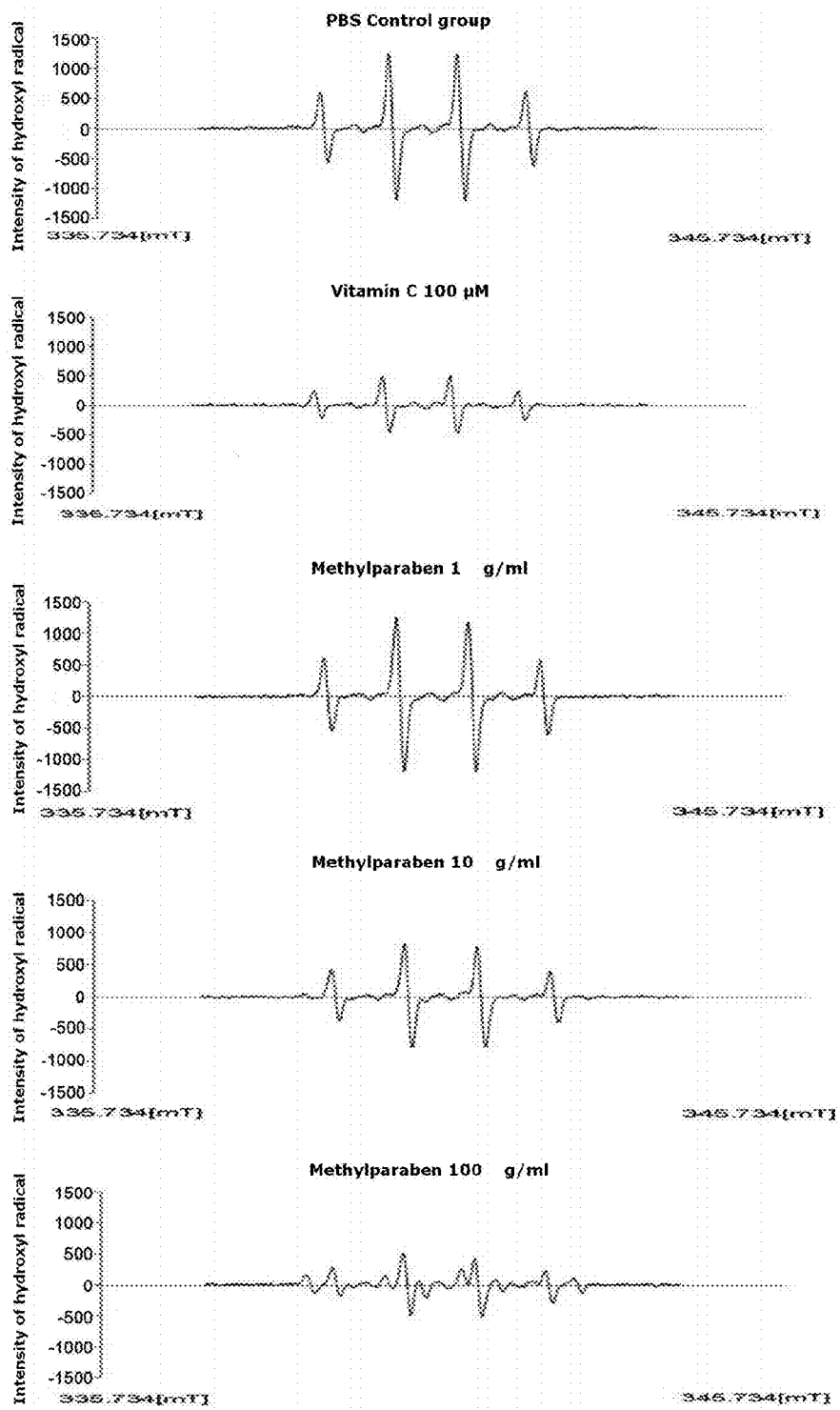
FIG. 2 is a graph showing results of measuring an amount of active oxygen in relation to a concentration of methylparaben by use of an ESR spectrometer.

In order to identify active oxygen removal ability of methylparaben (MP), Fenton reaction [$H_2O_2$+$FeSO_4$] was performed to derive hydroxyl radicals. The derived hydroxyl radicals were entrapped by a nitrone spin trap (DMPO) and the entrapped DMPO-OH addition product was measured by an electron spin resonance (ESR) spectrometer. ESR spectrum was measured by reacting a reaction reagent [phosphate buffer solution (pH 7.4); 4.5 M DMPO 10 µl, 0.6 mM $FeSO_4$ 75 µl, 2.8 M $H_2O_2$ 75 µl], methylparaben and vitamin C (VitC), then, using an ESR spectrometer (JES-FA, JEOL, Japan), and the measured results are shown in FIG. 2. In this regard, the ESR spectrometer carried out analysis using some parameters [magnetic field 340 mT, power 1.00 mW, frequency 9.19 GHz, amplitude modulation 0.2 mT, gain 200, scanning time 2 minutes, scanning width 10 mT, time constant 0.03 seconds, and temperature 20° C.].

As shown in FIG. 2, it was found from the analyzed results that adding methylparaben (MP) reduced an amount of active oxygen and the reduction in amount of the active oxygen was further increased as a concentration of the active oxygen was higher.

Figure 3:
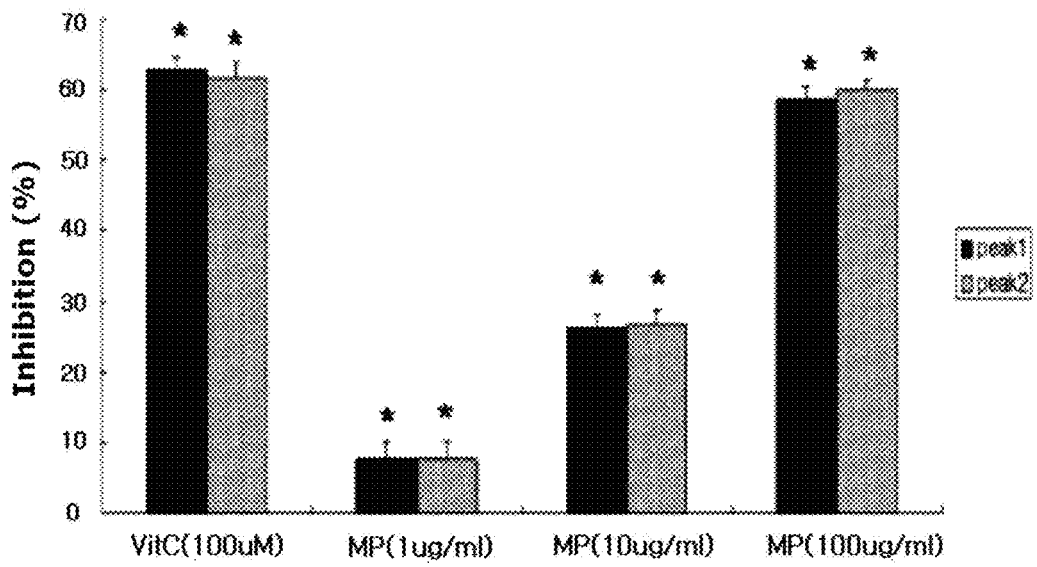
FIG. 3 is a graph showing active oxygen inhibitory ability in relation to a concentration of methylparaben.

In addition, FIG. 3 shows a level of active oxygen inhibitory ability to a concentration of methylparaben (MP), in the form of a mean value±mean error (n=4). The symbol (*) indicates a significant difference relative to a control group and this value is obtained by a one-way ANOVA test ($p<0.05$). As a result, when methylparaben (MP) was added, an active oxygen inhibitory ability was increased. Additionally, when a concentration of methylparaben (MP) was 100 µg/ml, it showed an active oxygen inhibitory ability substantially similar to that of VitC.

Example 3

Test for Cell Protective Activity to Alpha (α)-synuclein, Active Oxygen and Excitatory Brain Neurotransmitter In order to identify whether methylparaben (MP) in cultured cells has cell protective effects against active oxygen, excitatory brain neurotransmitter, and α-synuclein, a cell protective activity test was performed. These materials, that is, the active oxygen, excitatory brain neurotransmitter, and α-synuclein has been indicated as a cause of extensive damage of nerve cells with respect to Parkinson's disease and other degenerative cerebral disorders.

Figure 4:
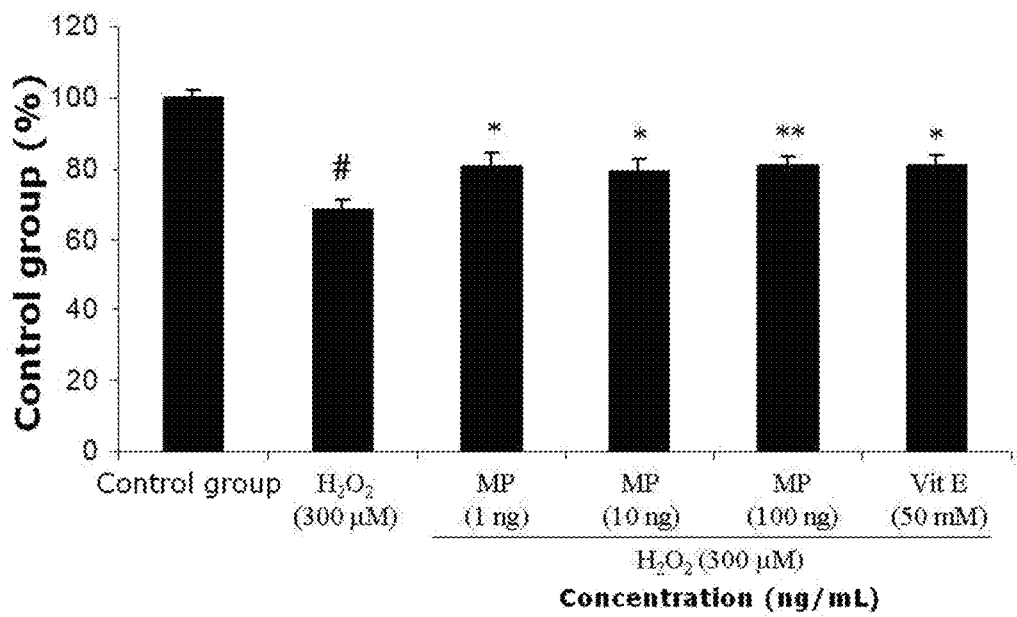
FIG. 4 is a graph illustrating cell protective effect of methylparaben in relation to active oxygen.
Figure 5:
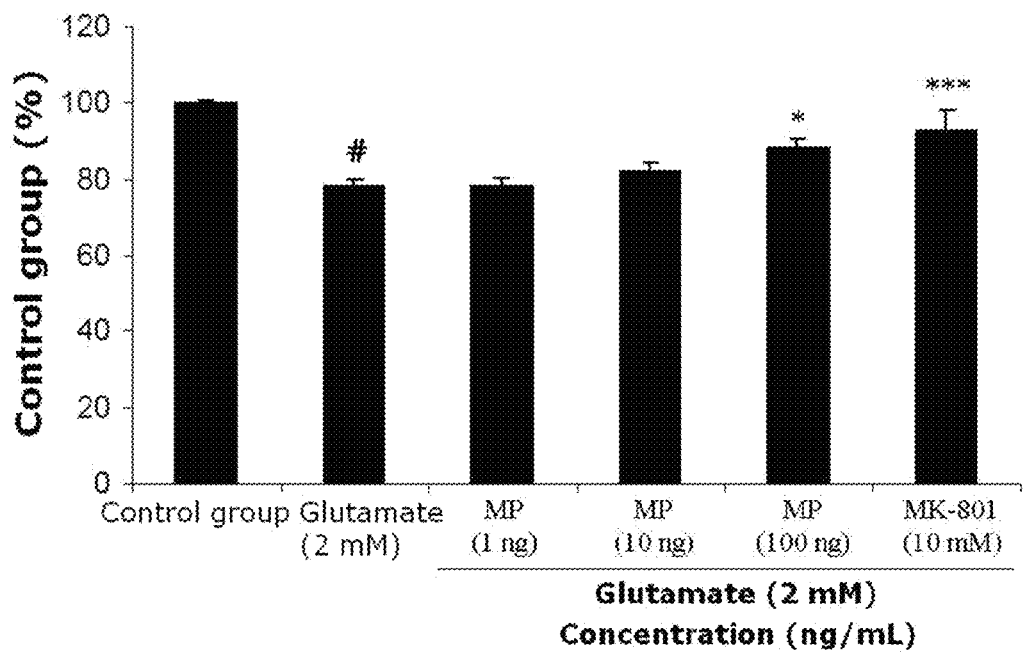
FIG. 5 is a graph illustrating cell protective effect of methylparaben in relation to an excitatory brain neurotransmitter.
Figure 6:
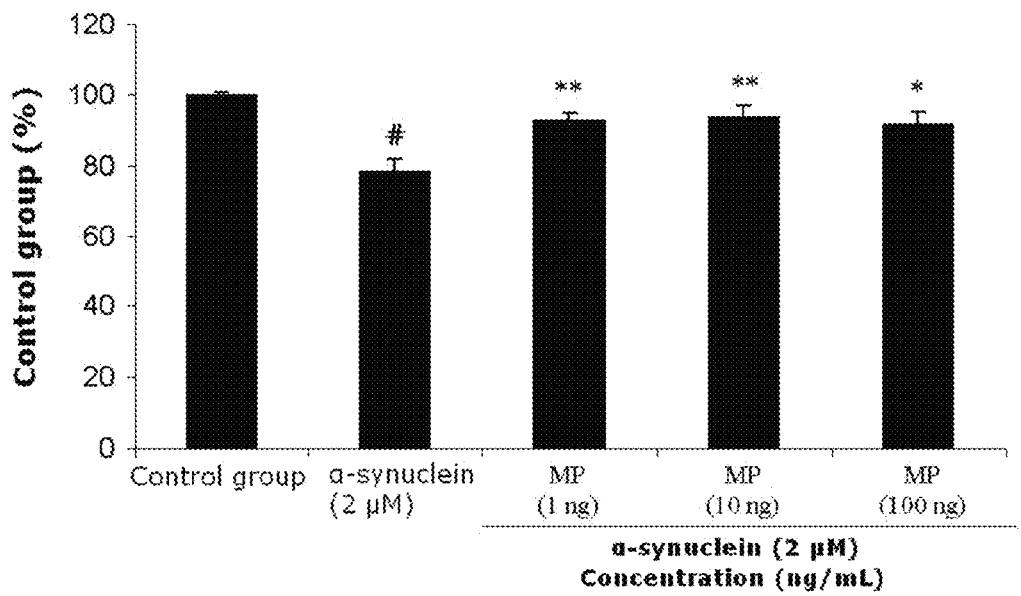
FIG. 6 is a graph illustrating cell protective effect of methylparaben in relation to α-synuclein.

Each well of a 96-well plate was provided with SH-SY5Y cells ($5\times10^3$ cells; 10% FBS added DMEM medium) derived from human nerve cancer and cultured at 37° C. for 24 hours. After this, 1, 10 and 100 ng/ml of methylparaben (MP), 50 µM Vitamin E (Vit E) or 10 µM MK-801 was added and further cultured for 4 hours. Alternatively, as a control group, a culture solution without the addition of a drug was prepared. After culturing for 4 hours, 300 mM hydrogen peroxide solution ($H_2O_2$) generating active oxygen, 2 mM glutamate as an excitatory brain neurotransmitter, and 2 µM α-synuclein were further added and cultured for 24 hours. After culturing, the cultured solution was washed using phosphate buffered saline (PBS). 100 µl cultured solution provided with a 10% cell proliferation reagent (WST-1) was poured into an incubator at 37° C. and reacted for 1 hour under cancer conditions, and then, absorbance was measured at 450 nm. Results of the measurements are shown in FIGS. 4 to 6. Herein, each of the measured values was represented in the form of a mean value±mean error (n=6).

The symbol (#) in FIGS. 4, 5 and 6 indicates a significant difference relative to the control group while (*) indicates a significant difference relative to an α-synuclein treatment group. These results are values obtained from a one-way ANOVA test ($p<0.05$). Also, the symbol () indicates a significant difference relative to the hydrogen peroxide treatment group, glutamate treatment group, or α-synuclein treatment group, and this result is a value obtained from the one-way ANOVA test ($p<0.01$). In addition, the symbol (*) indicates a significant difference relative to the hydrogen peroxide treatment group, glutamate treatment group, or α-synuclein treatment group, and this result is a value obtained from the one-way ANOVA test ($p<0.001$). Accordingly, it was found that, when 10, and 100 ng/ml of methylparaben (MP) was added, apoptosis caused by the active oxygen, excitatory brain neurotransmitter, and/or α-synuclein was significantly suppressed, as compared to the control group. It was also found that the above effect is substantially similar to 50 μM VitE or 10 μM MK-801 used as positive control groups. In other words, the above results demonstrated that methylparaben (MP) has cell protective effects against active oxygen, excitatory brain neurotransmitters, or α-synuclein and may be expected to exhibit effects of improving movement dysfunction and dementia symptoms in a Parkinson's disease model, on the basis of the above findings.

Example 4

Preparation of Parkinson's Disease Model

In order to verify the effects of methylparaben (MP) as a treatment drug of Parkinson's disease, an animal model with Parkinson's disease was prepared using dopamine hydroxide (6-OHDA). A C57BL/6 mouse weighing 20 to 25 g was used as a test animal. In the catecholamine nervous system, dopaminergic neurons were selectively destroyed and, as a pre-treatment of protecting noradrenaline neurons, 25 mg/kg of desipramine was intraperitoneally (i.p.) administered 1 hour before surgery. After anesthesia, the mouse was fixed on a stereotaxic instrumental device (David-Kopf frame) for test animals. Head skin was cut open to a diameter of about 2 cm and using an electric drill a small hole was formed in the right side of the skull. Dopamine hydroxide having a 10 μg/2.5 μl concentration mixed with 0.2% ascorbic acid was injected into the skull using a syringe (Hamilton). A coordinate for the right substantia nigra-corpus striatum was defined as AP+0.8 mm, ML−2.0 mm, DV−3.3 mm with reference to Paxinos and Watson's atlas. In order to prevent the dopamine hydroxide from flowing backward, this material was slowly injected over 5 minutes and the syringe was slowly removed, then, the head skin was stitched up. For a drug treatment group, 100 or 200 μg/kg of methylparaben (MP) and 10 mg/kg of deprenyl were i.p. administered 30 minutes before surgery and both of methylparaben (MP) and deprenyl were administered everyday for 2 weeks. For a normal control group, overall anesthesia and surgery processes were performed in the same manner as carried out for a Parkinson's disease-derived test group, except that a normal saline solution including 0.2% (w/v) ascorbic acid, which is a solvent containing dopamine hydroxide dissolved therein, was injected into the same surgical location.

Example 5

Rotarod Test

In order to identify whether methylparaben (MP) can improve movement dysfunction of the Parkinson's disease model, a rotarod test was performed and the test results were evaluated on day 14 after the surgery of Parkinson's disease. The rotarod test refers to a test of measuring a residence time when a mouse was riding on a rotarod without falling off. A rotation speed of the rotarod was set to 10 rpm and the rotarod test was performed over 10 minutes after an adaptation time of 5 minutes. A riding time on the rotarod was repeatedly measured three times and a mean value was calculated, then, a final value was represented in the form of the mean value±mean error (n=6).

Figure 7:
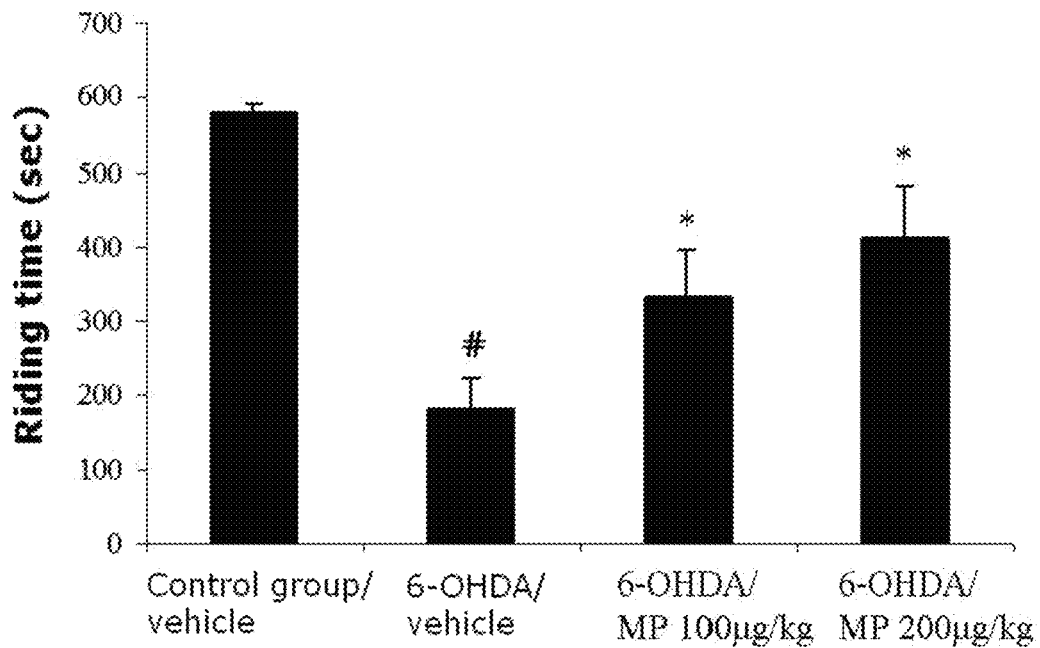
FIG. 7 is a graph illustrating improvement of movement dysfunction (week 1 and week 2 after surgery) by administration of methylparaben (100, and 200 µg/kg).

FIG. 7 shows effects of improving movement dysfunction by administration of methylparaben (MP) (100, and 200 μg/kg). The symbol (#) indicates a significant difference relative to the control group and this value was obtained from the one-way ANOVA test ($p<0.05$), while (*) indicates a significant difference relative to the dopamine hydroxide treatment group and this value was obtained from the one-way ANOVA test ($p<0.05$).

Example 6

Observation of Rotary Movement

As another verification method of Parkinson's disease treatment effect by methylparaben (MP) where mice having surgery according to the above procedures showed desired lesion formation on the substantia nigra-corpus striatum route and hemi-Parkinsonism, 0.5 mg/kg of apomorphine was subcutaneously (s.c) administered to the mice after 2 weeks, in order to carry out the selection. Rotary movement was evaluated in a hemi-sphere perplex equipped with a rotor motor and, after an adaptation time of 10 minutes, the mice were subject to measurement of the number of revolutions in ipsilateral and contralateral directions, respectively, for 1 hour after the administration of apomorphine. Each of the measured values was expressed as a mean value±mean error (n=6).

Figure 8:
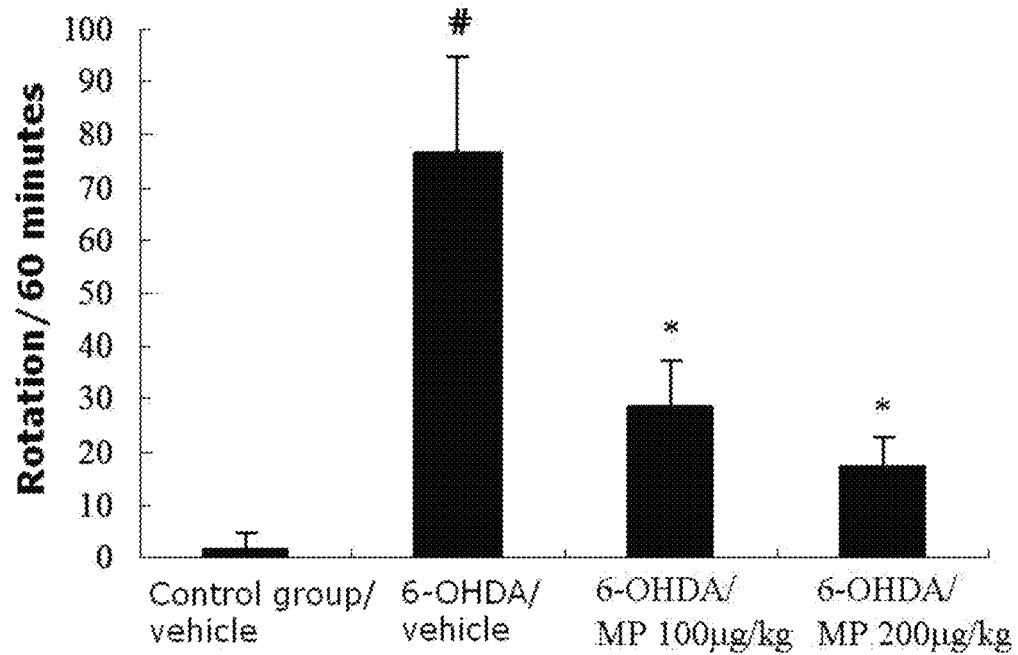
FIG. 8 is a graph illustrating improvement of turning movement dysfunction by administration of methylparaben (100, and 200 µg/kg).

FIG. 8 shows effects of improving rotary movement dysfunction by administration of methylparaben (MP) (100, and 200 μg/kg). The symbol (#) indicates a significant difference relative to the control group and this value was obtained from the one-way ANOVA test ($p<0.05$), while (*) indicates a significant difference relative to the dopamine hydroxide treatment group and this value was obtained from the one-way ANOVA test ($p<0.05$).

Example 7

Y-Shaped Maze Test

An Y-shaped maze measurement device has three extending arms to form an alphabet 'Y' shape wherein each arm has a length of 35 cm, height of 9 cm, and width of 5 cm, and all arms are formed at the same angle. After positioning a test animal to face an end of one of the arms of the Y-shaped maze, the animal was allowed to freely go around the arms for 8 minutes. Motions of the animal were recorded and, when the animal with hind legs moved inside the arm, the animal was deemed to pass the arm ('arm entry'). Movement of the animal was represented by the number of crossings ('alternation') and one alternation is defined to be when the animal continuously passes three arms. A quantity of spontaneous crossing movement is a percentage ratio of a practical alternation and a maximum possible alternation (that is, a total alternation −2).

Figure 9:
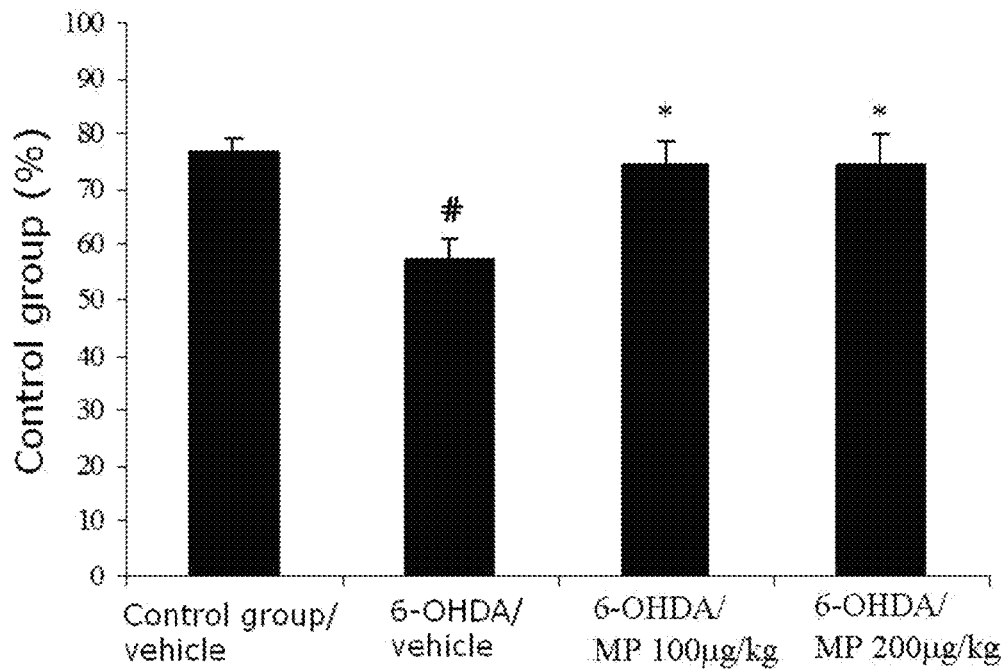
FIG. 9 is a graph illustrating enhancement of memory (Y-shaped maze test) by administration of methylparaben (100, and 200 µg/kg).

FIG. 9 shows effects of enhancing memory in a Y-shaped maze test by administration of methylparaben (MP) (100, and 200 μg/kg). The symbol (#) indicates a significant difference relative to the control group and this value was obtained from the one-way ANOVA test ($p<0.05$), while (*) indicates a significant difference relative to the dopamine hydroxide treatment group and this value was obtained from the one-way ANOVA test ($p<0.05$).

Example 8

Passive Avoidance Test

As a test device, a shuttle box having a size of 50×15×40 cm in width×length×height and being provided with an electrically conductive grid was used. The box was separated into two rooms, each having a size of 25×15 cm, by a connecting guillotine door (10×10 cm). Each room was illuminated using a 20 W light bulb. Noise was 60 dB or less and the test was performed in a room with very low illumination.

A mouse was placed in one room (A) of the two rooms separated by the door and the door was opened while turning on a light at 1500 lux. By doing this, the mouse looked around the room and entered the other room (B) without illumination. At this time, the door was operated to be automatically closed. By measuring a time taken from the opening of the door while turning on the light, to the closing of the door, a latency time was determined. The mouse may pass from room A to room B if the above process is repeated. If the mouse crossed from room A into room B within 20 seconds by repeating the above described process, a training process was deemed to be completed. On the next day, the trained mouse was placed in room A and, when the mouse crossed into room B, 0.25 mA current flowed for 2 seconds through a stainless steel grid mounted on the bottom of the room to give a shock to soles of the feet of the mouse, while turning off the light.

The mouse may develop a memory of a relation between the dark room and the foot-shock. As such, when placing the mouse in room A after 24 hours, the mouse may be at a loss as to whether to enter room B, even if room B is lighted. Here, a latency time was compared. After 1 day, a time taken from placing the above mouse in room A just before the mouse crossed into room B when a light turned on, was measured. A maximum measurement time was 5 minutes.

Figure 10:
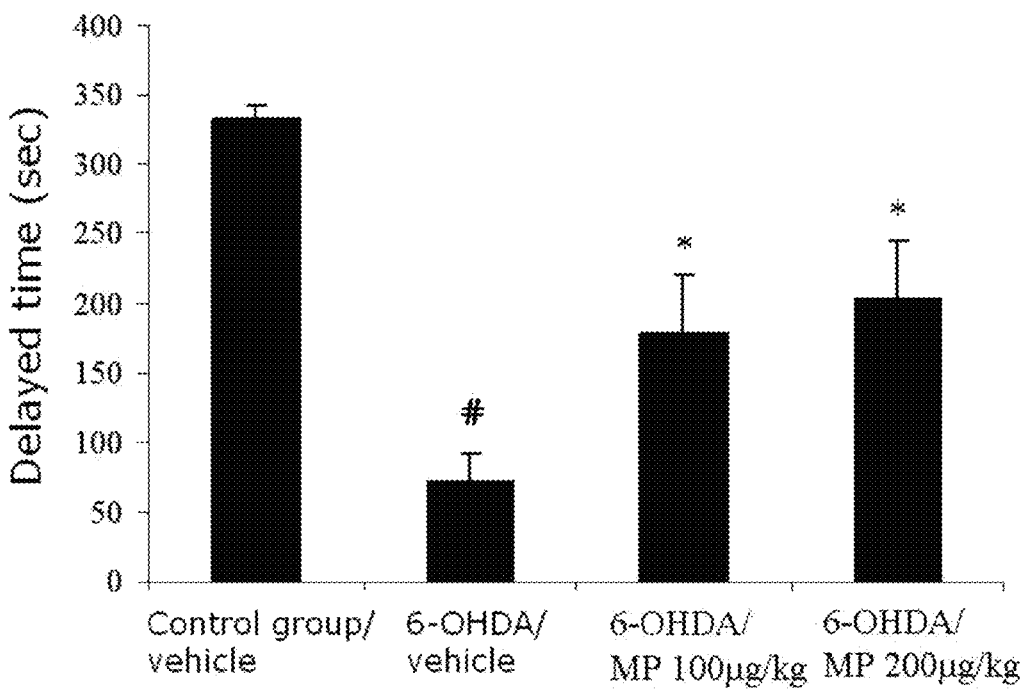
FIG. 10 is a graph illustrating enhancement of memory (passive avoidance test) by administration of methylparaben (100, and 200 µg/kg).

FIG. 10 shows effects of enhancing memory in the passive avoidance test by administration of methylparaben (MP) (100, and 200 µg/kg). The symbol (#) indicates a significant difference relative to the control group and this value was obtained from the one-way ANOVA test ($p<0.05$), while (*) indicates a significant difference relative to the dopamine hydroxide treatment group and this value was obtained from the one-way ANOVA test ($p<0.05$).

As shown in FIGS. 7 to 10, it was identified that the methylparaben (MP) administration groups (100, and 200 µg/kg) have effects of significantly improving deteriorated movement ability and memory by preparation of a Parkinson's disease model, compared to the control group. Based on such results, it can be understood that methylparaben (MP) has antioxidant activity and neuron protective activity against toxic materials generated by degenerative neurological brain disorders, thereby exhibiting effects of enhancing deteriorated memory caused by movement dysfunction and symptoms of dementia disorders.

The invention claimed is:

1. A method for treatment of Parkinson's disease, the method comprising administering to a subject in need thereof a therapeutically effective amount of at least one compound selected from the group consisting of methylparaben and ethylparaben.

2. The method according to claim 1, wherein the compound is methylparaben.

3. The method according to claim 1, wherein the compound is formulated into granulates, powders, syrups, solutions, suspensions, tablets, capsules, troches, pills, injections, or suppositories.

\* \* \* \* \*